United States Patent [19]

Kaneko et al.

[11] Patent Number: 5,256,800

[45] Date of Patent: Oct. 26, 1993

[54] OPTICALLY ACTIVE 2,2-DIMETHYL-1,3-DIOXIN-4-ONES AND METHOD FOR PREPARING SAME

[75] Inventors: Chikara Kaneko; Masayuki Sato, both of Sendai, Japan

[73] Assignee: Chisso Corporation, Osaka, Japan

[21] Appl. No.: 836,425

[22] Filed: Feb. 18, 1992

[30] Foreign Application Priority Data

Feb. 21, 1991 [JP] Japan ................... 3-047285

[51] Int. Cl.$^5$ ............................................ C07D 319/06
[52] U.S. Cl. ..................... 549/274; 549/273; 549/292; 549/294; 549/518; 549/561
[58] Field of Search ............. 549/273, 274, 292, 294, 549/518, 561

[56] References Cited

PUBLICATIONS

Sakaki et al.; J.C.S., C.C.; 1991; pp. 434–435.
Sato et al; Chem. Abst.; 1992; 41376.
Sakaki et al.; Tetrahedron; Asymmetry; vol. 2 No. 5; 1991; pp. 343–346.
Sakaki et al., Chemistry Letters, No. 6, Jun. 1990, pp. 901–904.
Chisso Corp., Patent Abstracts of Japan, vol. 14, No. 439 (C-761), 19 Sep. 1990 [JP-A-2 171 192 2 Jul. 1990].
Sakaki et al., Tetrahedron, vol. 47, No. 32, pp. 6197–6214 (1991).

*Primary Examiner*—Marianne M. Cintins
*Assistant Examiner*—Michael B. Hydorn
*Attorney, Agent, or Firm*—Wenderoth, Lind & Ponack

[57] ABSTRACT

There are provided novel and optically active 2,2-dimethyl-1,3-dioxin-4-ones which are useful as starting materials for physiologically active compounds, functional materials or the like. Furthermore, a method for preparing an optically active compound comprises reacting a racemic 1,3-dioxin-4-one with vinylacetate in the presence of lipase to resolve the racemic compound into optically active compound represented by the formula (3)

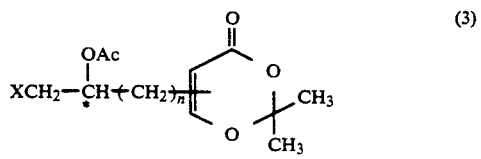

and an optically active compound represented by the formula (4)

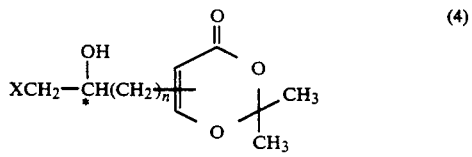

which is an antipode of the compound represented by the formula (3).

3 Claims, No Drawings

OPTICALLY ACTIVE 2,2-DIMETHYL-1,3-DIOXIN-4-ONES AND METHOD FOR PREPARING SAME

BACKGROUND OF THE INVENTION

2. Field of the Invention

The present invention relates to optically active 1,3-dioxin-4-ones which are useful as starting materials for physiologically active compounds, functional materials and the like, and a method for preparing the same.

2. Description of the Prior Art

As compounds of 1,3-dioxin-4-ones, racemic compounds represented by the formula

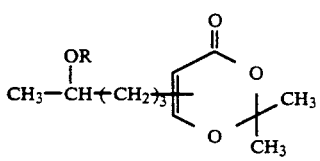

are described in B. Damin., J. Org. Chem., 46 (17), 3552 (1981) and N. A. Petasis., J. Chem. Soc., Chem, Commun., 11, 836 (1990), but optically active compounds analogous to these compounds have not been known.

On the other hand, in order to obtain physiologically active compounds, functional materials and the like, optically active compounds are necessary as starting materials. For example, in the case that the physiologically active compound, the functional material or the like has an asymmetric carbon atom, plural isomers are present, but usually one of these isomers has advantageous characteristics. Therefore, when a racemic modification or a compound having a low optical purity is used as the starting material, the resultant product cannot exert sufficient physiological activity or functional properties. Thus, it is desired that the compound which will be fed as the starting material also has the sufficient optical purity.

SUMMARY OF THE INVENTION

In view of the above-mentioned problems, an object of the present invention is to provide novel and optically active 1,3-dioxin-4-ones which are useful as starting materials for physiologically active compounds, functional materials or the like.

Another object of the present invention is to provide a method for preparing these novel and useful compounds.

The present inventors have repeatedly and intensively researched to achieve the above-mentioned objects, and as a result, they have succeeded in obtaining novel and optically active 1,3-dioxin-4-ones, and the present invention has been completed.

An optically active 1,3-dioxin-4-one which is the first aspect of the present invention is characterized by having the formula (1):

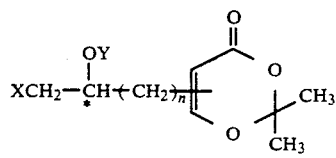
(1)

A method for preparing an optically active compound which is the second aspect of the present invention is characterized by reacting a racemic 1,3-dioxin-4-one represented by the formula (2)

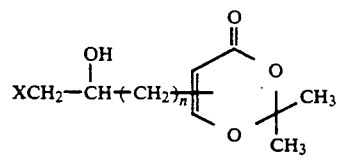
(2)

with vinyl acetate in the presence of lipase to resolve the racemic compound into an optically active compound represented by the formula (3)

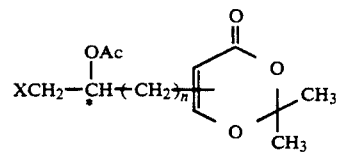
(3)

and an optically active compound represented by the formula (4)

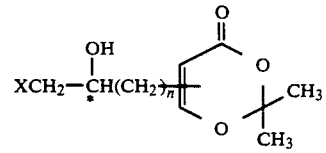
(4)

which is an antipode of the compound represented by the formula (3).

A method for preparing an optically active compound which is the third aspect of the present invention is characterized by hydrolyzing a racemic 1,3-dioxin-4-one represented by the formula (5)

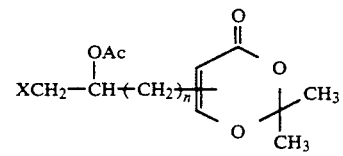
(5)

in the presence of lipase to resolve the racemic compound into an optically active compound represented by the formula (3) and an optically active compound represented by the formula (4) which is an antipode of the compound represented by the formula (3).

A method for preparing an optically active 1,3-dioxin-4-one which is the fourth aspect of the present invention is characterized by bringing a compound represented by the formula (6)

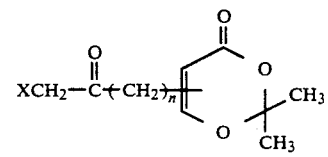
(6)

into contact with baker's yeast to sterically and selectively reduce this compound and to thereby form an optically active 1,3-dioxin-4-one.

In the formulae (1) to (6), n is a value of 1 to 3, X is a hydrogen atom, a benzyloxy group, a chlorine atom or N₃, and Y is a hydrogen atom or an acetyl group. The substituent in each formula is present at the 5-position or 6-position. When n is 1, X is the benzyloxy group, the chlorine atom or N₃, and the substituent is present at the 6-position. When n is 2, X is the hydrogen atom, and the substituent is present at the 5-position. And when n is 3, X is the hydrogen atom, and the substituent is present at the 6-position. The symbol * represents an asymmetric carbon atom.

DETAILED DESCRIPTION OF THE INVENTION

Compounds represented by the formulae (2), (5) and (6) which are starting materials for use in a manufacturing method of the present invention can be suitably prepared in accordance with the following route, for example, in the case of n=1:

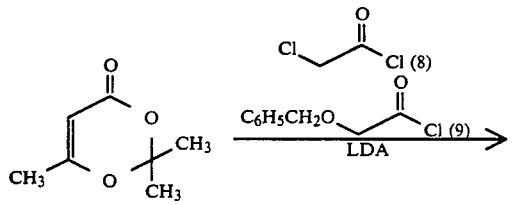

(7)

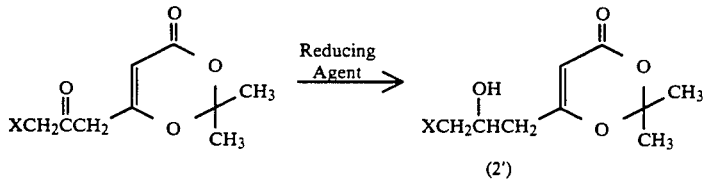

(6) (n = 1, X = C₆H₅CH₂O or Cl)

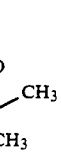 NaN₃

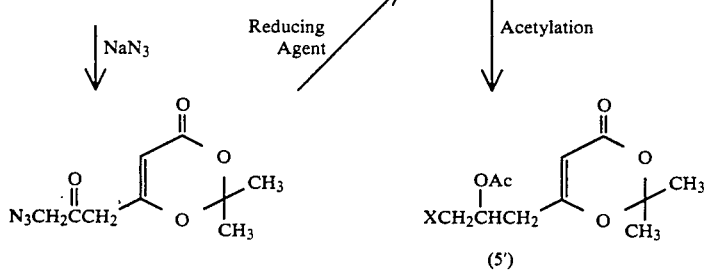

(6) (in the case of n = 1 and X = N₃)

That is, 2,2,6-trimethyl-1,3-dioxin-4-one (7) is reacted with chloroacetyl chloride (8) or benzyloxyacetyl chloride (9) in the presence of a base typified by lithium-diisopropylamide (LDA) to derive an acyl compound [having the formula (6) in which n is 1, and X is a benzyloxy group or a chlorine atom], and the acyl compound is then reacted with sodium azide (NaN₃) in dimethylformamide (DMF) to obtain an azide [having the formula (6) in which n is 1 and X is N₃]. This product can be used as a material for an asymmetrical reduction using baker's yeast. Next, the compound of the formula (6) is reacted with a reducing agent such as sodium borohydride or lithium aluminum hydride to carry out a reduction reaction, whereby a racemic compound represented by the formula (2') is derived.

Furthermore, the compound represented by the formula (2') is reacted with a acetylating agent such as acetyl chloride or acetic anhydride in the presence of a basic catalyst such as pyridine, triethylamine or dimethylaminopyridine to carry out acetylation, so that a racemic compound represented by the formula (5') is formed. These compounds represented by the formulae (2') and (5') can be used as starting materials for the preparation of the optically active compounds of the second and third aspects of the present invention.

For example, in the case of compounds having the formulae (2), (5) and (6) in which n is 3, the reaction is as follows:

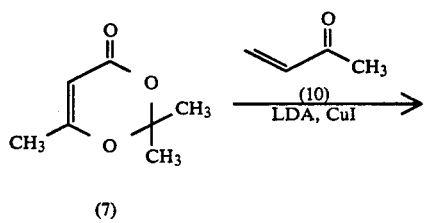

(7)

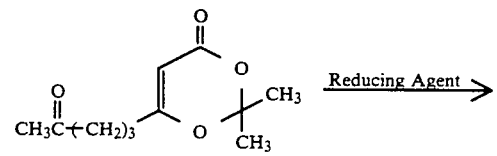

(6)

-continued

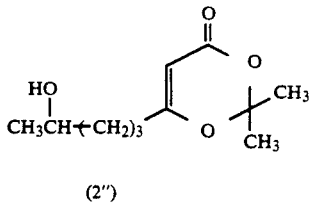

(2″)

That is, 2,2,6-trimethyl-1,3-dioxin-4-one (7) is reacted with α,β-unsaturated ketone (10) in the presence of a base such as LDA and copper iodide to form a compound having a formula (6) in which n is 3. This compound can further be subjected to a reduction reaction using a reducing agent such as sodium borohydride or lithium aluminum hydride, thereby deriving a racemic compound represented by the formula (2″).

Reference will be made to a method for preparing the optically active compound of the second aspect of the present invention.

The compound of the formula (2) is reacted with vinyl acetate (11) in the presence of lipase to selectively acylate either antipode alone and to thereby resolve the compound into an optically active ester compound of the formula (3) and an optically active alcoholic compound which is represented by the formula (4) and which is an antipode of the compound having the formula (3), as follows:

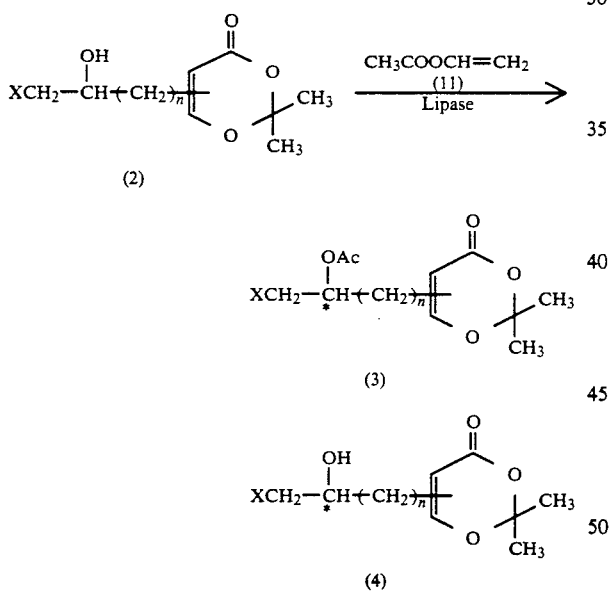

In the above-mentioned preparation process, any kind of lipase can be used, so long as it has the ability by which either antipode is selectively and exclusively acylated, and above all, Lipase MY (made by The Meito Sangyo Co., Ltd.; origin *Candida cylindracea*) and Lipase PS (made by Amano Pharmaceutical Co., Ltd., origin *Pseudomonas fluorescens*) are preferable. A preferable reaction solvent is benzene, but the reaction can be carried out without using any solvent. A reaction temperature may be room temperature, and a reaction time is from 4 to 9 hours.

After the reaction has been carried out in this way, lipase can be removed by a usual filtration, but it can be reutilized as it is. The reaction product obtained in the form of the filtrate can be separated into an optically active alcoholic compound represented by the formula (4) and an optically active ester compound which is represented by the formula (3) and which is the antipode of the compound having the formula (4) by operation such as vacuum distillation or column chromatography. Furthermore, the optically active ester compound of the formula (3) obtained above is deacetylated by hydrolysis using lipase to obtain an optically active alcohol which is the antipode of the above-mentioned optically active alcoholic compound.

Reference will be made to a method for preparing the optically active compound of the third aspect of the present invention.

A racemic compound represented by the formula (5) can be used as a starting material and subjected to a stere selective hydrolysis reaction to resolve the racemic compound into optically active compounds represented by the formulae (3) and (4), as follows:

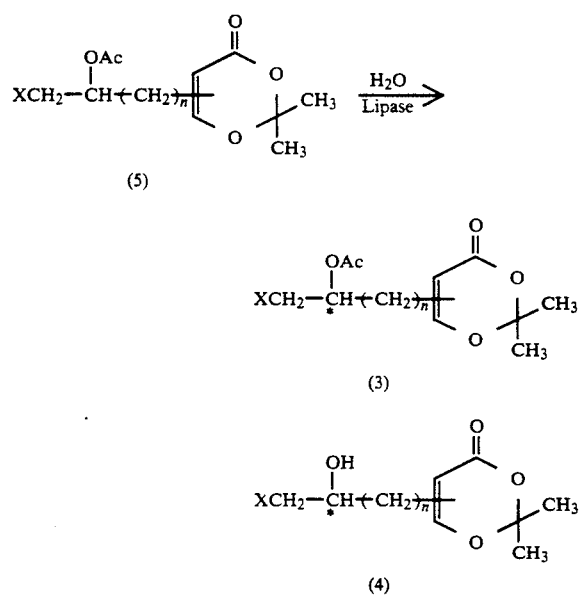

Either antipode of the compound of the formula (5) can be selectively and exclusively hydrolyzed by the action of lipase in a phosphoric acid buffer solution to resolve the compound into the optically active compounds represented by the formulae (3) and (4). Any kind of lipase can be here used, so long as it has the ability by which either antipode is selectively and exclusively hydrolyzed, and above all, Lipase MY (made by The Meito Sangyo Co., Ltd.; origin *Candida cylindracea*) and Lipase PS (made by Amano Pharmaceutical Co., Ltd., origin *Pseudomonas fluorescens*) are preferable. The phosphoric acid buffer solution which can be used preferably has a pH of about 7.2, and it can be mixed with about 30% of acetone.

After this reaction, the resultant reaction product can be taken out by a usual extraction and then subjected to vacuum distillation or column chromatography to resolve it into the optically active alcoholic compound represented by the formula (4) and the optically active ester compound of the formula (3), and the obtained optically active ester compound of the formula (3) can be deacetylated by hydrolysis using lipase to obtain an optically active alcohol which is the antipode of the above-mentioned optically active alcoholic compound.

Reference will be made to a method for preparing an optically active 1,3-dioxin-4-one of the fourth aspect of the present invention.

A compound represented by the formula (6) is subjected to a stereo selective reduction reaction using baker's yeast as an asymmetrical reducing agent to derive a 1,3-dioxin-4-one represented by the formula (1) in which Y is H, as follows:

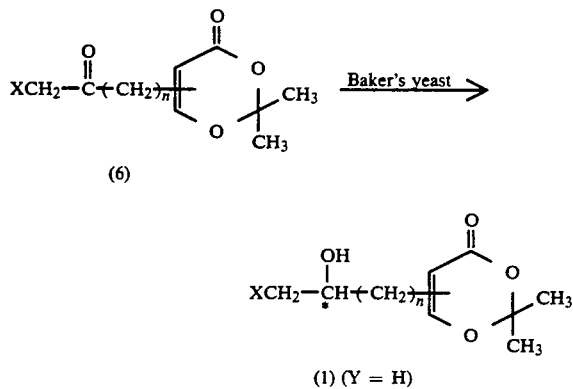

As the asymmetrical reducing agent which can be used in the present invention, the baker's yeast (*Saccharomyces cerevisiae*) is preferable, but any kind of reducing agent can be employed, so long as it can act on a substrate and achieve the asymmetrical reduction reaction (e.g., *Kloechera saturnus, Lipomyces starkeyi, Saccharomyces delbrueckii, Saccharomyces fermentati, Candida humicola, Candida guillermondi* and *Candida albicans*).

The asymmetrical reduction using the baker's yeast can be achieved by effectively bringing the baker's yeast into contact with the substrate and a carbon source usually in water, and this reaction can be carried out in an open system without using any special reaction devices. Furthermore, water which can be used in the reaction may be tap water, and any particular treatment is not required for water. Preferable examples of the carbon source include carbohydrates such as saccharose and glucose, and an organic acid such as acetic acid and an alcohol can also be used on occasion.

In the present invention, the reaction temperature is suitably from 15° to 45° C., and the particularly preferable reaction temperature is from 25° to 35° C., depending upon the kind of substrate to be used. The reaction time is suitably from 1 to 100 hours, similarly depending upon the kind of substrate. The concentration of the substrate is suitably from 0.01 to 20% by weight, preferably from 0.5 to 5% by weight.

The removal of the desired product from the reaction product obtained through the asymmetrical reduction can be effectively achieved by extraction with an organic solvent such as dichloromethane, chloroform or ethyl acetate. Furthermore, the extracted reaction product can be purified by a usual organic chemical procedure such as recrystallization or column chromatography.

The compound of the formula (1) which can be prepared by the method of the present invention is useful as a starting material for a physiologically active compound.

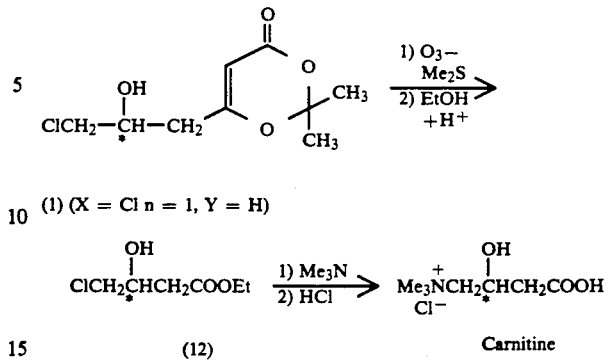

That is, the compound having the formula (1) in which X is Cl, n is 1, and Y is a hydrogen atom can be easily converted into ethyl 4-chloro-3-hydroxybutanoate (12) by ozone oxidation and then esterification, as shown by the above-mentioned chemical formulae. This compound of the formula (12) can be converted into carnitine in accordance with a process described in C. J. Sir et al., J. Org. Chem. Soc., 105, 5925 (1983).

When the (+) form or the (−) form of the optically active compound of the starting material represented by the formula (12) is suitably selected, L-carnitine or D-carnitine can be selectively obtained. It is known that L-carnitine functions to accelerate the internal, secretion from the digestive organ and to lower the blood sugar value and the cholesterol value in blood, and in short L-carnitine functions to normalize metabolism. Thus, it is fair to say that L-carnitine is a useful compound.

In addition, the compound of the formula (1) in which n is 3 can be easily converted into an eight-membered ring ether compound (13) by heating the same at 100° C. in toluene, as shown by the following reaction formula. This compound of the formula (13) is the central skeleton of natural compounds in the ocean such as lorencin, laurenyne, laurepinnacin and pinnatifidenyne to which much attention has been paid in recent years. These useful oceanic natural compounds and similar compounds can be synthesized by utilizing the procedure of the present invention.

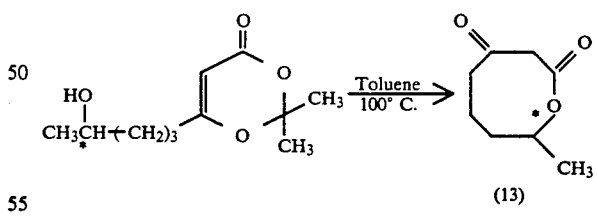

(1) (X = H, n = 3, and y = H).
[N. A. Petasis et al., J. Chem. Soc., Chem. Commun., 11, 836 (1990)].

The present invention can provide novel compounds of optically active 1,3-dioxin-4-ones represented by the formula (1), and a method for preparing the same. These compounds are useful as starting materials for physiologically active compounds and functional materials.

Now, the present invention will be described in detail in reference to examples. It is to be noted that the scope of the present invention should not be limited to these examples.

EXAMPLE 1

Asymmetrical reduction reaction of 2,2-dimethyl-6-(3-chloro-2-oxopropyl)-1,3-dioxin-4-one [a compound having the formula (6) in which n is 1, X is Cl, and the substituent is present at the 6-position] by the use of baker's yeast:

[First Step] Synthesis of 2,2-dimethyl-6-(3-chloro-2-oxopropyl)-1,3-dioxin-4-one [a compound having the formula (6) in which n is 1, X is Cl, and the substituent is present at the 6-position]:

In an argon gas stream, 20.6 ml of n-butyl lithium (1.6M solution in hexane) were added to 60 ml of an ether solution containing 3.53 g (0.033 mol) of diisopropylamine at −20° C. to form LDA. After stirring for 30 minutes, a mixture of 4.26 g (0.03 mol) of 2,2-dimethyl-6-methyl-1,3-dioxin-4-one and 60 ml of ether as well as 60 ml of an ether solution containing 1.69 g (0.015 mol) of chloroacetyl chloride were added to LDA. After the temperature was gradually returned to room temperature, 10% hydrochloric acid was added thereto to neutralize the solution, and extraction was then carried out with ether. The resultant organic layer was dried over anhydrous magnesium sulfate. Next, the solvent was distilled off, and the residue was then subjected to column chromatography (an eluent of hexane:ethyl acetate =4:1), thereby obtaining 2.26 g (yield 69%) of 2,2-dimethyl-6-(3-chloro-2-oxopropyl)-1, 3-dioxin-4-one.

m.p. 64.5° to 65° C.

Elementary Analysis:

Calcd.: C 49.42%; H 5.07%; Cl 16.23%.

Found: C 49.46%; H 5.11%; Cl 16.40%.

IR(CHCl$_3$): 1730 1645 cm$^{-1}$ $^1$H-NMR (CDCl$_3$) δ : 1.73 (6H, s), 3.59 (2H, s), 4.18 (2H, s), 5.40 (1H, s)

[Second Step] Asymmetrical reduction of 2,2-dimethyl-6-(3-chloro-2-oxopropyl)-1,3-dioxin-4-one by the use of baker's yeast:

30 g of baker's yeast (made by Oriental Yeast Co., Ltd.) and 15 g of saccharose were added in 30 ml of tap water, and the solution was then stirred at 32° C. for 30 minutes. Afterward, 300 mg of 2,2-dimethyl-6-(3-chloro-2-oxopropyl)-1,3-dioxin-4-one obtained in the above-mentioned first step were added thereto, and the solution was then stirred at the same temperature overnight. 7.5 g of saccharose were further added thereto, followed by stirring overnight. Water of the reaction solution was then distilled off under reduced pressure, and the resultant residue was extracted with dichloromethane and then dried over anhydrous sodium sulfate. Afterward, the solvent was distilled off, and the residue was then subjected to column chromatography (an eluent of hexane:ethyl acetate TM 4:1), thereby obtaining 106 mg (yield 35%) of (−)-2,2-dimethyl-6-(3-chloro-2-hydroxypropyl)-1,3-dioxin-4-one [a compound having the formula (1) in which n is 1, X is Cl, Y is a hydrogen atom, and the substituent is present at the 6-position].

$[\alpha]_D^{24}$ 8.9° (c 0.65, CHCl$_3$)

IR(CHCl$_3$): 3160, 1725, 1640 cm$^{-1}$ $^1$H-NMR (CDCl$_3$) δ : 1.87 (6H, s), 2.52 (2H, d), 2.87-3.29 (1H, br), 3.62 (2H, d), 4.18 (1H t t), 5.40 (1H, s)

According to measurement by HPLC using CHIRALCEL OD (Daisel Chemical Industries, Ltd.), it was confirmed that the optical purity of the product was 46% ee.

EXAMPLE 2

Asymmetrical reduction reaction of 2,2-dimethyl-6-(3-benzyloxy-2-oxopropyl)-1,3-dioxin-4-one [a compound having the formula (6) in which n is 1, X is a benzyloxy group, and the substituent is present at the 6-position] by the use of baker's yeast:

[First Step] Synthesis of 2,2-dimethyl-6-(3-benzyloxy-2-oxopropyl)-1,3-dioxin-4-one:

In an argon gas stream, 13.75 ml of n-butyl lithium (1.6M solution in hexane) were added to 60 ml of an ether solution containing 2.35 g (0.022 mol) of diisopropylamine at −20° C. to form LDA. After stirring for 30 minutes, the solution was cooled to −78° C., and 6.93 ml (0.04 mol) of HMPA were added thereto, followed by stirring for 15 minutes. Afterward, a mixture of 2.84 g (0.02 mol) of 2,2-dimethyl-6-methyl-1,3-dioxin-4-one and 60 ml of ether as well as 60 ml of an ether solution containing 1.85 g (0.01 mol) of benzyloxyacetyl chloride were added to LDA. After the temperature was gradually returned to room temperature, 10% hydrochloric acid was added thereto to neutralize the solution, and extraction was then carried out with ether. The resultant organic layer was dried over anhydrous magnesium sulfate. Next, the used solvent was distilled off, and the residue was then subjected to column chromatography (an eluent of hexane:ethyl acetate =4:1), thereby obtaining 1.95 g (yield 67%) of 2,2-dimethyl-6-(3-benzyloxy-2-oxopropyl)-1,3-dioxin-4-one.

IR(CHCl$_3$): 1735, 1645 cm$^{-1}$ $^1$H-NMR (CDCl$_3$) δ : 1.76 (6H, s), 3.50 (2H, s), 4.11 (2H, s), 4.73 (2H, s), 5.33 (1H, s), 7.36 (6H s)

[Second Step] Asymmetrical reduction of 2,2-dimethyl-6-(3-benzyloxy-2-oxopropyl)-1,3-dioxin-4-one by the use of baker's yeast:

30 g of baker's yeast (made by Oriental Yeast Co., Ltd.) and 15 g of saccharose were added in 30 ml of tap water at 32° C., and the solution was then stirred for 30 minutes. Afterward, 300 mg of 2,2-dimethyl-6-(3-benzyl-2-oxopropyl)-1,3-dioxin-4-one were added thereto, and the solution was then stirred overnight at the same temperature. 7.5 g of saccharose were further added thereto, followed by stirring overnight. Water of the reaction solution was then distilled off under reduced pressure, and the residue was extracted with dichloromethane and then dried over anhydrous sodium sulfate. Afterward, the solvent was distilled off, and the residue was then subjected to column chromatography (an eluent of hexane:ethyl acetate=4:1), thereby obtaining 168 mg (yield 56%) of (−)-2,2-dimethyl-6-(3-benzyloxy-2-hydroxypropyl)-1,3-dioxin-4-one [a compound having the formula (1) in which n is 1, X is a benzyloxy group, Y is the hydrogen atom, and a substituent is present at the 6-position].

$[\alpha]_D^{24}$ −8.72° (c 1.81, CHCl$_3$)

IR(CHCl$_3$): 3450, 1730, 1640 cm$^{-1}$ $^1$H-NMR (CDCl$_3$) δ : 1.66 (6H, s), 2.40 (2H, d), 3.35-3.83 (2H, m), 3.50 (1H, br), 3.95-4.24 (1H, m), 4.56 (2H, s), 5.33 (1H, s), 7.33 (5H, s)

According to measurement by HPLC using CHIRALCEL OD (made by Daisel Chemical Industries, Ltd.), it was confirmed that the optical purity of the product was 75% ee.

EXAMPLE 3

Asymmetrical reduction reaction of 2,2-dimethyl-6-(3-azido-2-oxopropyl)-1,3-dioxin-4-one [a compound having the formula (6) in which n is 1, X is N$_3$ and the substituent is present at the 6-position] by the use of baker's yeast: [First Step] Synthesis of 2,2-dimethyl-6-(3-azido-2-oxopropyl)-1,3-dioxin-4-one:

195 mg (3.0 mmol) of sodium azide were added to 2 ml of a DMF solution containing 328 mg (1.5 mmol) of 2,2-dimethyl-6-(3-chloro-2-oxopropyl)-1,3-dioxin-4-one prepared in Example 1, followed by stirring at room temperature for 10 minutes. Afterward, the solution was poured into ice water, extracted with ether, and then dried with anhydrous magnesium sulfate. After ether was distilled off, the residue was then subjected to column chromatography (an eluent of hexane:ethyl acetate=1:1), thereby obtaining 278 mg (yield 82%) of 2,2-dimethyl-6-(3-azido-2-oxopropyl)-1,3-dioxin-4-one.

IR(CHCl$_3$): 2125, 1730, 1645 cm$^{-1}$ $^1$H-NMR (CDCl$_3$) δ : 1.72 (6H, s), 3.42 (2H, s), 4.05 (2H, s), 5.73 (1H, s) [Second Step] Asymmetrical reduction of 2,2-dimethyl-6-(3-azido-2-oxopropyl)-1,3-dioxin-4-one by the use of baker's yeast:

30 g of baker's yeast (made by Oriental Yeast Co., Ltd.) and 15 g of saccharose were added in 30 ml of tap water, and the solution was then stirred at 32° C. for 30 minutes. Afterward, 300 mg of 2,2-dimethyl-6-(3-azido-2-oxopropyl)-1,3-dioxin-4-one were added thereto, and the solution was then stirred overnight at the same temperature. 7.5 g of saccharose were further added thereto, followed by stirring overnight. Water of the reaction solution was then distilled off under reduced pressure, and the residue was extracted with dichloromethane and then dried over anhydrous sodium sulfate. Afterward, the solvent was distilled off, and the resultant residue was then subjected to column chromatography (an eluent of hexane:ethyl acetate=4:1), thereby obtaining 67 mg (yield 22%) of (+)-2,2-dimethyl-6-(3-azido-2-hydroxypropyl)-1,3-dioxin-1,3-dioxin-4-one [a compound having the formula (1) in which n is 1, X is N$_3$, Y is a hydrogen atom, and the substituent is present at the 6-position].

$[α]_D^{24}$ +4.35° (c 1.93, CHCl$_3$)

IR(CHCl$_3$): 2110, 1725, 1640 cm$^{-1}$ $^1$H-NMR (CDCl$_3$) δ : 1.66 (6H, s), 2.45 (2H, d), 2.93 (1H, br), 3.23-3.63 (2H, m), 3.83-4.36 (1H, m), 5.36 (1H, s)

According to measurement by HPLC using CHIRALCEL OD (made by Daisel Chemical Industries, Ltd.), it was confirmed that the optical purity of the product was 17% ee.

EXAMPLE 4

Optical resolution of (±)-2,2-dimethyl-6-(3-chloro-2-hydroxypropyl)-1,3-dioxin-4-one [a compound having the formula (6) in which n is 1, X is Cl and, the substituent is present at the 6-position]:

A mixture of 7.0 g (31.8 mmol) of (±)-2,2-dimethyl-6-(3-chloro-2-hydroxypropyl)-1,3-dioxin-4-one, 7.0 g of Lipase PS (Amano Pharmaceutical Co., Ltd.), 2.7 g (31.8 mmol) of vinyl acetate and 500 ml of benzene was stirred at 28° C. for 7 days. Afterward, lipase was removed by filtration under suction, and the solution was then subjected to silica gel chromatography (an eluent of hexane:vinyl acetate=5:1 and later 3:1), thereby obtaining 4.12 g (yield 51%) of (+)-2,2-dimethyl-6-(3-chloro-2-hydroxypropyl)-1,3-dioxin-4 -one (a compound having the formula (1) in which n was 1, X was Cl, Y was a hydrogen atom, and the substituent was present at the 6-position) having $[α]_D^{20}$ +19.0° (c 1.10, CHCl$_3$) and 2.44 g (yield 36%) of (+)-2,2-dimethyl-6-(3-chloro-2-acetoxypropyl)-1,3-dioxin-4-one [a compound having the formula (1) in which n was 1, X was Cl, Y was Ac, and the substituent was present at the 6-position] having $[α]_D^{20}$ +0.2° (c 1.07, CHCl$_3$)

IR(CHCl$_3$): 1730, 1645 cm$^{-1}$ $^1$H-NMR (CDCl$_3$) δ : 1.71 (6H, s), 2.11 (3H, d), 2.67 (2H, d), 3.66 (2H, d), 5.07-5.53 (1H, m), 5.35 (1H, s)

According to measurement by HPLC using CHIRALCEL OD and CHIRALCEL OJ (made by Daisel Chemical Industries, Ltd.) of optical resolution columns, it was confirmed that the optical purities of these products were 96% ee and 95% ee, respectively.

Furthermore, a mixture of 900 mg (3.43 mmol) of (+)-2,2-dimethyl-6-(3-chloro-2-acetoxypropyl)-1, 3-dioxin-4-one obtained above, 900 mg of Lipase MY and 150 ml of a 0.1M phosphoric acid buffer solution was stirred at 28° C. for 3 days. The solution was extracted with ethyl acetate and then dried over anhydrous magnesium sulfate. Afterward, the solvent was distilled off, and the residue was then subjected to column chromatography (an eluent of hexane:ethyl acetate=3:1), thereby obtaining 594 mg (yield 79%) of (−)-2,2-dimethyl-6-(3-chloro-2-hydroxypropyl)-1,3-dioxin-4-one (a compound having the formula (1) in which n was 1, X was Cl, Y was a hydrogen atom, and the substituent was present at the 6-position). According to measurement by HPLC using CHIRALCEL OD and CHIRALCEL OJ (made by Daisel Chemical Industries, Ltd.) of optical resolution columns, it was confirmed that the optical purity of the product was 98% ee.

EXAMPLE 5

Optical resolution of (±)-2,2-dimethyl-6-(3-chloro-2-hydroxypropyl)-1,3-dioxin-4-one [a compound having the formula (2) in which n was 1, X was Cl, and the substituent was present at the 6-position]:

A mixture of 7.0 g of (±)-2,2-dimethyl-6-(3-chloro-2-hydroxypropyl)-1,3-dioxin-4-one, 7.0 g of Lipase MY (made by The Meito Sangyo Co., Ltd.), 2.7 g (31.8 mmol) of vinyl acetate and 500 ml of benzene was stirred at 28° C. for 9 days. After removal of lipase by filtration under suction, the solution was subjected to silica gel chromatography (an eluent of hexane:ethyl acetate=5:1 and later 3:1), thereby obtaining 3.81 g (yield 55%) of (−)-2,2-dimethyl-6-(3-chloro-2-hydroxypropyl)-1,3-dioxin-4-one [a compound having the formula (1) in which n was 1, X was Cl, Y was the hydrogen atom, and a substituent was present at the 6-position] having $[α]_D^{20}$ −8.4° (c 1.02, CHCl$_3$)

and 1.63 g (yield 24%) of (+)-2,2-dimethyl-6-(3-chloro-2-acetoxypropyl)-1,3-dioxin-4-one [a compound having the formula (1) in which n was 1, X was Cl, Y was Ac, and the substituent was present at the 6-position] having $[α]_D$ +0.4° (c 1.66, CHCl$_3$)

IR(CHCl$_3$): 1730, 1645 cm$^{-1}$ $^1$H-NMR (CDCl$_3$) δ : 1.71 (6H, s), 2.11 (3H, d), 2.67 (2H, d), 3.66 (2H, d), 5.07-5.53 (1H, m), 5.35 (1H, s)

According to measurement by HPLC using CHIRALCEL OD and CHIRALCEL OJ (made by Daisel Chemical Industries, Ltd.) of optical resolution columns, it was confirmed that the optical purities of these products were 49% ee and 95% ee, respectively.

EXAMPLE 6

Optical resolution of (±)-2,2-dimethyl-6-(3-chloro-2-hydroxypropyl)-1,3-dioxin-4-one [a compound having the formula (2) in which n was 1, X was Cl, and the substituent was present at the 6-position]:

A mixture of 7.0 g of (±)-2,2-dimethyl-6-(3-chloro-2-hydroxypropyl)-1,3-dioxin-4-one, 7.0 g of Lipase PS (made by Amano Pharmaceutical Co., Ltd.), and 500 ml of vinyl acetate was stirred at 28° C. for 7 days. After removal of lipase by filtration under suction, the solution was subjected to silica gel chromatography (an eluent of hexane:vinyl acetate=5:1 and later 3:1), thereby obtaining 3.86 g (yield 47%) of (+)-2,2-dimethyl-6-(3-chloro-2-hydroxypropyl)-1, 3-dioxin-4-one [a compound having the formula (1) in which n was 1, X was Cl, Y is a hydrogen atom, and the substituent was present at the 6-position] having $[\alpha]_D^{20}$ +19.3° (c 1.67, CHCl$_3$)

and 3.39 g (yield 49%) of (+)-2,2-dimethyl-6-(3-chloro-2-acetoxypropyl)-1,3-dioxin-4-one [a compound having the formula (1) in which n was 1, X was Cl, Y was Ac, and the substituent was present at the 6-position] having $[\alpha]_D$ +0.14° (c 1.20, CHCl$_3$)

IR(CHCl$_3$): 1730, 1645 cm$^{-1}$ $^1$H-NMR (CDCl$_3$) δ : 1.71 (6H, s), 2.11 (3H, d), 2.67 (2H, d), 3.66 (2H, d), 5.07–5.53 (1H, m), 5.35 (1H, s)

According to measurement by HPLC using CHIRALCEL OD and CHIRALCEL OJ (made by Daisel Chemical Industries, Ltd.) of optical resolution columns, it was confirmed that the optical purities of these products were 98% ee and 94% ee, respectively.

EXAMPLE 7

Optical resolution of (±)-2,2-dimethyl-6-(3-chloro-2-acetoxypropyl)-1,3-dioxin-4-one [a compound having the formula (5) in which n was 1, X was Cl, and the substituent was present at the 6-position]:

A mixture of 0.9 g (3.43 mmol) of (±)-2,2-dimethyl-6-(3-chloro-2-hydroxypropyl)-1,3-dioxin-4 -one, 0.9 g of Lipase PS, 150 ml of a 0.1M phosphoric acid buffer solution (pH 7.2) and 450 ml of acetone was stirred at 28° C. for 3 hours. After the product was extracted with ethyl acetate, the solvent was distilled off, and the residue was subjected to silica gel chromatography (an eluent of hexane:vinyl acetate=3:1), thereby obtaining 27 mg (yield 3%) of (−)-2,2-dimethyl-6-(3-chloro-2-hydroxypropyl)-1,3-dioxin-4-one [a compound having the formula (1) in which n was 1, X was Cl, Y was a hydrogen atom, and the substituent was present at the 6-position] and 0.48 g (yield 53%) of (−)-2,2-dimethyl-6-(3-chloro-2-acetoxypropyl)-1,3-dioxin-4-one [a compound having the formula (1) in which n was 1, X was Cl, Y was Ac, and the substituent was present at the 6-position].

EXAMPLE 8

Asymmetric reduction reaction of 2,2-dimethyl-6-(4-oxopentyl)-1,3-dioxin-4-one [a compound having the formula (6) in which n was 3, X was a hydrogen atom, and the substituent was present at the 6-position] by the use of baker's yeast: [First Step] Synthesis of 2,2-dimethyl-6-(4-oxopentyl)-1,3-dioxin-4-one:

In an argon gas stream, 20.6 ml of n-butyl lithium (1.6M solution in hexane) were added to 60 ml of an ether solution containing 3.53 g (0.033 mol) of diisopropylamine at −20° C. to form LDA. After stirring for 30 minutes, the solution was cooled to −78° C., and 10.4 ml (0.06 mol) of HMPA were added thereto, followed by stirring for 15 minutes. Afterward, a mixture of 4.26 g (0.03 mol) of 2,2-dimethyl-6-methyl-1,3-dioxin-4-one and 60 ml of ether as well as 60 ml of an ether solution containing 2.1 g (0.03 mol) of methyl vinyl ketone were added to the solution. After the temperature was gradually returned to room temperature, 10% hydrochloric acid was added thereto to neutralize the solution, and extraction was then carried out with ether. The resultant organic layer was dried over anhydrous magnesium sulfate. Next, the used solvent was distilled off, and the residue was then subjected to column chromatography (an eluent of hexane:ethyl acetate=4:1), thereby obtaining 3.16 g of 2,2-dimethyl-6-(4-oxopentyl)-1,3-dioxin-4-one.

EXAMPLE 9

[Second Step] Asymmetrical reduction of 2,2-dimethyl-6-(oxopentyl)-1,3-dioxin-4-one by the use of baker's yeast:

30 g of baker's yeast (made by Oriental Yeast Co., Ltd.) and 15 g of saccharose were added in 30 ml of tap water, and the solution was then stirred at 32° C. for 30 minutes. Afterward, 300 mg of 2,2-dimethyl-6-(4-oxopentyl)-1,3-dioxin-4-one were added thereto, and the solution was then stirred overnight at the same temperature. 7.5 g of saccharose were further added thereto, followed by stirring overnight. Water of the reaction solution was then distilled off under reduced pressure, and the resultant residue was extracted with dichloromethane and then dried over anhydrous sodium sulfate. Afterward, the solvent was distilled off, and the resultant residue wa then subjected to column chromatography (an eluent of hexane:ethyl acetate=4:1), thereby obtaining 148 mg (yield 50%) of (−)-2,2-dimethyl-6-(4-hydroxypentyl)-1,3-dioxin-4-one [a compound having the formula (1) in which n is 3, X is a hydrogen atom, Y is the hydrogen atom, and a substituent is present at the 6-position].

According to measurement by HPLC using CHIRALCEL OD (Daisel Chemical Industries, Ltd.), it was confirmed that the optical purity of the product was 90% ee or more.

EXAMPLE 10

Asymmetric reduction of 2,2-dimethyl-5-(3-oxobutyl)-1,3-dioxin-4-one by the use of baker's yeast:

30 g of baker's yeast (made by Oriental Yeast Co., Ltd.) and 15 g of saccharose were added in 30 ml of tap water, and the solution was then stirred at 32° C. for 30 minutes. Afterward, 350 mg of 2,2-dimethyl-5-(3-oxobutyl)-1,3-dioxin-4-one were added thereto, and the solution was then stirred overnight at the same temperature. 7.5 g of saccharose were further added thereto, followed by stirring overnight. Water of the reaction solution was then distilled off under reduced pressure, and the resultant residue was extracted with dichloromethane and then dried over anhydrous sodium sulfate. Afterward, the solvent was distilled off, and the residue was then subjected to column chromatography (an eluent of hexane:ethyl acetate=4:1), thereby obtaining 161 mg (yield 55%) of (−)-2,2-dimethyl-5-(3-hydroxybutyl)-1,3-dioxin-4-one [a compound having the formula (1) in which n is 2, X is a hydrogen atom, Y is a hydrogen atom, and the substituent is present at the 5-position].

According to measurement by HPLC using CHIRALCEL OD (Daisel Chemical Industries, Ltd.), it was confirmed that the optical purity of the product was 99% ee or more.

Example 10 (Application Example)

Preparation of optically active ethyl 4-chloro-3-hydroxybutanoate (12):

Ozone was introduced into a mixture of 225.5 mg (1 mmol) of (+)-2,2-dimethyl-(3-chloro-2-hydroxypropyl)-1,3-dioxin-4-one (96% ee) obtained in Example 4 and 20 ml of methanol at −78° C. for 5 hours, and 2 ml of dimethyl sulfide were added thereto, followed by stirring at the same temperature for 2 hours. The temperature was gradually returned to room temperature, and the solution was then stirred for 5 hours. Afterward, the solvent was distilled off, and the resultant residue was then dissolved in ethanol. 3 drops of concentrated sulfuric acid were added thereto, and the solution was then heated at 80° C. for 30 minutes. Next, ethanol was distilled off, and the residue was diluted with water. The solution was extracted with dichloromethane and then dried over anhydrous sodium sulfate, and the solvent was distilled off and the residue was then subjected to column chromatography (an eluent of hexane:ethyl acetate=5:1), thereby obtaining 109.4 mg (yield 66%) of (+)-ethyl 4-chloro-3-hydroxybutanoate.

$[\alpha]_D^{26}$ +21.1° (c 3.11, CHCl$_3$)

Furthermore, (-)-2,2-dimethyl-(3-chloro-2-hydroxypropyl)-1,3-dioxin-4-one (98% ee) obtained in Example 4 was used as a material in accordance with a similar reaction to form (-)-ethyl -4-chloro-3-hydroxybutanoate.

$[\alpha]_D^{24}$ −20.2° (c 1.00, CHCl$_3$)

What is claimed is:

1. An optically active 1,3-dioxin-4-one represented by the formula:

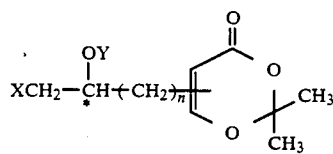

(1)

wherein n is a value of 1 to 3, X is a benzyloxy group, a chlorine atom or N$_3$, Y is a hydrogen atom or an acetyl group, and the substituent is present at the 5-position or 6-position; when, n is 1, X is the benzyloxy group, the chlorine atom or N$_3$, and the substituent is present at the 6-position; when n is 2, X is the hydrogen atom, and the substituent is present at the 5-position; and when n is 3, X is the hydrogen atom, and the substituent is present at the 6-position; and the symbol * represents an asymmetric carbon atom.

2. A method for preparing an optically active compound which is characterized by reacting a racemic 1,3-dioxin-4-one represented by the formula (2)

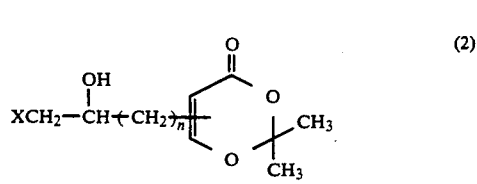

(2)

with vinyl acetate in the presence of lipase to resolve the racemic compound into an optically active compound represented by the formula (3)

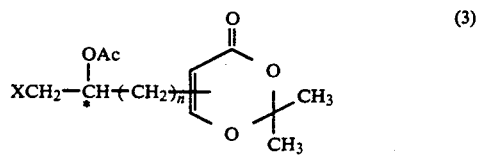

(3)

and an optically active compound represented by the formula (4)

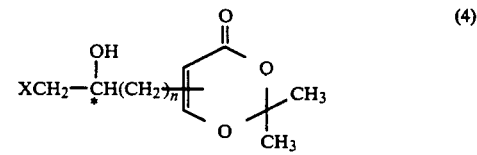

(4)

which is an antipode of the compound represented by the formula (3) wherein in the formulae (2), (3) and (4), n is a value of 1 to 3, X is a hydrogen atom, a benzyloxy group, a chlorine atom or N$_3$, Ac is an acetyl group, and the substituent is present at the 5-position or 6-position; when n is 1, X is the benzyloxy group, the chlorine atom or N$_3$, and the substituent is present at the 6-position; when n is 2, X is the hydrogen atom, and the substituent is present at the 5-position; and when n is 3, X is the hydrogen atom, and the substituent is present at the 6-position; and the symbol * represents an asymmetric carbon atom.

3. A method for preparing an optically active compound which is characterized by hydrolyzing a racemic 1,3-dioxin-4-one represented by the formula (5)

$$\text{XCH}_2-\underset{*}{\text{CH}}(\text{OAc})-(\text{CH}_2)_n-\text{(1,3-dioxin-4-one ring with CH}_3\text{, CH}_3\text{)} \quad (5)$$

in the presence of lipase to resolve the racemic compound into an optically active compound represented by the formula (3) and an optically active compound represented by the formula (4) which is an antipode of the compound represented by the formula (3) in the formulae (3), (4) and (5), n is a value of 1 to 3, X is a hydrogen atom, a benzyloxy group, a chlorine atom or N$_3$, Ac is an acetyl group, and the substituent is present at the 5-position or 6-position; when n is 1, X is the benzyloxy group, the chlorine atom or N$_3$, and the substituent is present at the 6-position; when n is 2, X is the hydrogen atom, and the substituent is present at the 5-position; and when n is 3, X is the hydrogen atom, and the substituent is present at the 6-position; and the symbol * represents an asymmetric carbon atom.

* * * * *